(12) United States Patent
von Schoenebeck et al.

(10) Patent No.: US 9,175,448 B2
(45) Date of Patent: Nov. 3, 2015

(54) DRUM HOUSING FOR A WORKING DRUM OF A CONSTRUCTION MACHINE OR MINING MACHINE, CONSTRUCTION MACHINE OR MINING MACHINE, AS WELL AS METHOD FOR MONITORING THE CONDITION OF A WORKING DRUM OF A CONSTRUCTION MACHINE OR MINING MACHINE

(75) Inventors: Winfried von Schoenebeck, Vettelschoss (DE); Joerg Berges, Hennef (DE); Peter Berghoff, Windhagen (DE); Stefan Wagner, Bad Honnef (DE); Cyrus Barlmani, Königswinter (DE); Günter Hähn, Königswinter (DE)

(73) Assignee: Wirtgen GmbH (DE)

( * ) Notice: Subject to any disclaimer, the term of this patent is extended or adjusted under 35 U.S.C. 154(b) by 570 days.

(21) Appl. No.: 13/438,297

(22) Filed: Apr. 3, 2012

(65) Prior Publication Data

US 2012/0256470 A1 Oct. 11, 2012

(30) Foreign Application Priority Data

Apr. 6, 2011 (DE) .......................... 10 2011 016 271

(51) Int. Cl.
*E01C 23/088* (2006.01)

(52) U.S. Cl.
CPC .................................... *E01C 23/088* (2013.01)

(58) Field of Classification Search
USPC ........... 299/36.1, 39.1, 39.2, 39.4; 404/90–94
See application file for complete search history.

(56) References Cited

U.S. PATENT DOCUMENTS

| 4,006,936 A | | 2/1977 | Crabiel | |
| 4,325,580 A | * | 4/1982 | Swisher et al. | 299/39.8 |
| 4,655,634 A | * | 4/1987 | Loy et al. | 404/84.05 |

(Continued)

FOREIGN PATENT DOCUMENTS

| AT | 382683 B | 3/1987 |
| DE | 3411892 A1 | 10/1985 |

(Continued)

OTHER PUBLICATIONS

Liang et al., Vision-Based Automatic Tool Wear Monitoring System, Jun. 25-27, 2008, Proceedings of the 7th World Congress on Intelligent Control and Automation, Chongqing, China, pp. 6031-6035.

(Continued)

*Primary Examiner* — Sunil Singh
(74) *Attorney, Agent, or Firm* — Lucian Wayne Beavers; Patterson Intellectual Property Law, PC

(57) ABSTRACT

In a drum housing for a working drum of a construction machine or mining machine, the working drum being provided with tools and rotating about a drum axis, with a housing shell which at least partially encloses the circumference of the working drum, and with at least one inspection opening for a monitoring device arranged in the housing shell, wherein the monitoring device inspects the condition of the working drum or the tools thereof, it is provided for the following features to be achieved: a closing mechanism is arranged on the outside of the housing shell, the closing mechanism enabling closure of the at least one inspection opening.

27 Claims, 6 Drawing Sheets

(56) References Cited

U.S. PATENT DOCUMENTS

| | | |
|---|---|---|
| 4,903,780 A | 2/1990 | Barbieri |
| 5,474,397 A * | 12/1995 | Lyons .................... 299/39.5 |
| 6,149,342 A | 11/2000 | Phillips |
| 6,201,567 B1 | 3/2001 | Kuroda |
| 6,887,013 B2 | 5/2005 | Ley et al. |
| 6,923,508 B2 * | 8/2005 | Holl et al. ................ 299/39.4 |
| 6,990,390 B2 | 1/2006 | Groth et al. |
| 7,259,872 B2 | 8/2007 | Mullikin |
| 7,422,391 B2 | 9/2008 | Holl et al. |
| 7,905,682 B2 | 3/2011 | Holl et al. |
| 8,386,196 B2 | 2/2013 | Wagner et al. |
| 8,794,869 B2 | 8/2014 | Schlenker et al. |
| 2004/0146353 A1 | 7/2004 | Ley et al. |
| 2005/0207841 A1 | 9/2005 | Holl et al. |
| 2008/0153402 A1 | 6/2008 | Arcona et al. |
| 2009/0035064 A1 | 2/2009 | Holl et al. |
| 2010/0076697 A1* | 3/2010 | Wagner et al. ................ 702/34 |
| 2011/0121633 A1 | 5/2011 | Hall et al. |
| 2012/0256470 A1 | 10/2012 | von Schoenebeck et al. |
| 2013/0087172 A1 | 4/2013 | Roetsch |

FOREIGN PATENT DOCUMENTS

| | | |
|---|---|---|
| DE | 3218754 C2 | 11/1985 |
| DE | 3411892 C2 | 6/1986 |
| DE | 3505408 A1 | 8/1986 |
| DE | 3616170 A1 | 3/1987 |
| DE | 3818213 A1 | 11/1989 |
| DE | 3921875 A1 * | 1/1991 |
| DE | 10015005 A1 | 10/2001 |
| DE | 10203732 A1 | 8/2003 |
| DE | 102005016346 B3 | 1/2007 |
| EP | 1039036 A2 | 9/2000 |
| EP | 1396581 B1 | 3/2004 |
| JP | H941863 A | 2/1997 |

OTHER PUBLICATIONS

European Search Report in EP 12 15 8064, Aug. 2, 2012 (3 pages).
Caterpillar Operation & Maintenance Manual, PR-1000 Pavement Profiler, Jul. 1990, 78 pages.
ARRA Basic Asphalt Recycling Manual, U.S. Department of Transportation Federal Highway Administration, 2001, 108 pages.

* cited by examiner

DRUM HOUSING FOR A WORKING DRUM OF A CONSTRUCTION MACHINE OR MINING MACHINE, CONSTRUCTION MACHINE OR MINING MACHINE, AS WELL AS METHOD FOR MONITORING THE CONDITION OF A WORKING DRUM OF A CONSTRUCTION MACHINE OR MINING MACHINE

CROSS-REFERENCE TO RELATED APPLICATIONS

The present invention claims the priority of German Patent Application no. DE 10 2011 016 271.2 filed on Apr. 6, 2011, the disclosures of which are incorporated herein by reference.

BACKGROUND OF THE INVENTION

1. Field of the Invention

The invention relates to a drum housing for a working drum of a construction machine or mining machine, said working drum being provided with tools and rotating about a drum axis with a specified rotating direction, a construction machine or mining machine with such drum housing, as well as a method for monitoring the condition of a working drum of a construction machine/mining machine or of the tools thereof arranged on the circumference of the working drum by measuring the condition of the working drum or the tools thereof by means of a monitoring device.

2. Description of the Prior Art

Such a method is known from DE 10 2008 045 470 A1 (US 2010/0076697). A monitoring device monitors the condition of the tools of a road milling machine by means of at least one inspection opening in a housing shell of a drum housing, said housing shell at least partially enclosing the circumference of the working drum.

The working drum of a construction machine, which is provided with tools and rotates about a drum axis, such as a milling drum during the working of road surfaces by means of road milling machines, as well as for the mining of deposits by means of surface miners, is subject to a continuous process of wear and tear, wherein a tool breakage may also occur. This concerns mainly the tools used, and in particular the milling tools, but also the toolholders. When the tools reach a certain state of wear, it is advisable to replace the tools as the ongoing process will otherwise lose in efficiency. In this regard, a distinction needs to be made between different states of wear which lead to the replacement of a milling tool or toolholder respectively:

1. Replacement of the milling tool as there is no longer sufficient wear material, especially carbide metal in the tip. The penetration resistance becomes too great, which leads to the efficiency decreasing as a result of excessive friction loss. Wear and tear is mainly rotationally symmetrical.
2. Replacement of the toolholder as between the milling tool and holder, at the contact surface between these parts, wear and tear in particular of the holder occurs and the wear limit has been reached. This type of wear and tear is usually symmetrical.
3. Non-rotationally symmetrical wear and tear of the milling tool tip and/or the milling tool head caused by insufficient rotational movement of the milling tool during the milling process. This results in a poor milling pattern and the risk of a tool breakage as the supporting effect of the milling tool head is lost.
4. Furthermore, the toolholder may be subject to additional, non-rotationally symmetrical wear and tear.
5. Milling tool breakage.

Furthermore, worn-out and/or broken milling tools can result in secondary damage to the toolholders, or worn-out toolholders, respectively, can result in secondary damage to the milling drum. Timely replacement of the milling tools and/or toolholders can therefore be necessary and reduce costs. Replacing the milling tools and/or toolholders too early, on the other hand, also means not working at optimal cost. In such a case, existing wear potential is not utilized appropriately. Previously, without any monitoring device, the state of wear of the milling drum and the tools, namely, the milling tools and toolholders, was assessed by means of a visual check performed by the machine operator. To do so, the machine operator needs to switch off the machine (turn off engine and uncouple drum from the drive train). He then needs to open the rear drum plate in order to visually inspect the milling drum.

The milling drum is then turned by means of a second drive (auxiliary drive) in order to be able to inspect, section by section, the entire milling drum. The task of inspecting the drum may also be undertaken by a second operator. In the process, the state of wear of the toolholders is usually assessed via so-called wear markings, while the state of wear of the milling tools is assessed via the wear in tool length and the rotational symmetry of the wear pattern.

Checking the state of wear of the milling tool and holder is very time-consuming and reduces the operating time of the machine. In addition, there is the risk, owing to the highly subjective assessment, that the state of wear of the holder and milling tool is not assessed correctly and the wear potential is therefore not optimally utilized.

According to the known prior art apparent from FIG. 2, a barrel of the inspection camera of the monitoring device is guided into the interior of the drum housing through an inspection opening in the housing shell of the drum housing. Furthermore, it is provided that the monitoring device is stowed in a protection device during the milling process. Owing to the circulating milled material, the barrel inside the drum housing is subject to a high degree of wear and tear and may be severely damaged by larger fragments of the milled material. Furthermore, damage to the optics of the camera through the barrel cannot be excluded if the camera is not demounted during the milling operation. The replacement of damaged parts is time-consuming. In addition, mounting time is incurred by the stowing, or mounting respectively, of the monitoring device.

SUMMARY OF THE INVENTION

It is therefore the object of the invention to create a drum housing, a construction machine or mining machine, as well as a method for monitoring the condition of a working drum in which a monitoring device can be used at any time without any mounting effort and allows economy of time in the inspection of working drums.

The invention specifies a drum housing for a working drum of a construction machine or mining machine, said working drum being provided with tools and rotating about a drum axis, with a housing shell which at least partially encloses the circumference of the working drum. The housing shell has at least one inspection opening for a monitoring device arranged in the housing shell, wherein said monitoring device inspects the condition of the working drum or the tools thereof. A closing mechanism is arranged on the outside of the housing shell, enabling closure of the at least one inspection opening.

The invention provides in an advantageous manner, for the purpose of inspecting the condition of the working drum or the tools thereof, to open one or several inspection openings in the drum housing for inspection or to close said inspection openings during the working operation. In the opened state of the at least one inspection opening, inspections can be performed by means of the monitoring device. The monitoring device (for example, at least one inspection camera and preferably at least one light source, or an ultrasonic sensor or a scanner, for example, a laser scanner, or a camera without additional light source) can remain in its mounted state and does not have to be demounted during the milling operation. As nothing protrudes into the drum housing, nothing can be damaged. It is possible to clean the working drum with water, for example, prior to inspection in order to be able to perform the inspection even more effectively on a working drum, or the tools thereof, freed from dirt. To perform the inspection, the closing mechanism is moved into its opened position so that the at least one inspection opening is released for an optical path of the monitoring device. Following completion of the inspection, the at least one inspection opening can be closed again by operating the closing mechanism so that the milling operation can be resumed immediately afterwards unless the inspection has resulted in the necessity of a tool replacement.

It is preferably provided that the at least one inspection opening in the housing shell extends in longitudinal direction of the working drum. In this way, the inspection camera can scan the working drum linearly in longitudinal direction of the working drum. Accordingly, the light source, provided that such is required, can illuminate the working drum linearly, with the light source being directed at the measuring range of the inspection camera. For example, the at least one inspection opening may extend parallel to the drum axis.

A preferred embodiment of the invention provides that the at least one inspection opening tapers radially towards the working drum. Such a design of the inspection opening simplifies closing and opening because no parts of the closing mechanism can jam in the openings.

The monitoring device comprises at least one sensor device, for example, an inspection camera, and preferably one illuminating device, wherein the at least one inspection opening may comprise at least one first opening for the sensor device and, as the case may be, at least one second opening for the illuminating device.

The closing mechanism may comprise one each insert element adapted to the inspection opening in a complementary fashion, said insert element engaging with the inspection opening to close the inspection opening. The insert element adapted in a complementary fashion offers the advantage of fully closing the inspection opening. In this arrangement, the insert element closes the inspection opening in a positive-fitting fashion and tightly in such a way that almost no milled material can come through the inspection opening of the drum housing during the milling operation. The insert element closes in a preferably flush fashion towards the inside of the drum housing. The insert element may also comprise a wearing plate or wearing surface towards the inside of the drum housing in order to prevent wear and tear of the insert element.

One or several insert elements may be arranged on a support plate, or all insert elements may be arranged on a joint support plate, wherein the at least one support plate is relocatable into an opened position or into a closed position for the purpose of opening or closing the at least one inspection opening. Relocating may be understood as any type of movement, for example, pivoting, shifting, rotating, or a combination thereof.

The support plate may comprise at least one passage opening adapted to an inspection opening, said passage opening allowing, in the opened position of the closing mechanism, the passage of light beams and/or measuring beams of the monitoring device through the at least one passage opening of the support plate and the at least one inspection opening in the housing shell. In this case, the passage opening of the support plate and the at least one inspection opening overlap at least partially. The required movement lift of the support plate can thus be reduced.

The at least one insert element may be supported radially outwards in the closed position of the closing mechanism. In this way, the pressure on the insert element, which is generated by the milled material rotating in the drum housing, can be safely held. The insert element may either be directly supported radially outwards or may be mounted on a support plate which, in turn, is supported radially outwards.

The closing mechanism may comprise a locking mechanism, wherein the at least one support plate is lockable, in the closed position of the closing mechanism, in radial direction by means of the locking mechanism. The locking mechanism has the advantage that, in the locked position, the forces acting radially outwards are supported on the support plate at the drum housing and can thus not act on other elements of the closing mechanism, for example, on drive elements.

The closing mechanism may comprise a first drive mechanism and, optionally, a second drive mechanism, wherein the first drive mechanism relocates the at least one insert element between the closed position and opened position on the outside of the housing shell, and the second drive mechanism operates the locking mechanism. The drive mechanisms, for example, piston cylinder units, can be operated from the operator's platform so that opening or closing of the inspection openings can be effected fully automatically from the operator's platform of the construction machine.

When moved in closing direction, the first drive mechanism may push the at least one insert element, which is supported by the support plate, into the at least one inspection opening by means of at least one wedge-shaped limit stop mounted on the housing shell and one leading edge at the front end of the support plate when seen in the direction of movement, said leading edge being adapted to the wedged shape of the limit stop.

The at least one insert element and the corresponding inspection opening comprise slanted sides adapted to one another in such a fashion that the first drive mechanism, when moved in opening direction, moves the at least one insert element out of the at least one inspection opening. In doing so, the sides adapted to one another may glide on top of one another.

Several inspection openings and corresponding closing mechanisms may be arranged next to one another across the width of the working drum. This is of advantage in particular in wide working drums with a working width of, for example, more than half a meter in length.

The locking mechanism comprises at least one device supported at the drum housing which, in the closed position of the closing mechanism, supports the at least one support plate, in the closed position of the latter, in a positive-fitting fashion radially outwards and, in the opened position of the closing mechanism, releases the at least one support plate for displacing.

The at least one inspection opening may comprise two opening edges extending in longitudinal direction of the working drum, wherein at least the first opening edge, when seen in the direction of rotation of the working drum, may comprise a deflector bar. Said deflector bar serves the purpose of slightly deflecting the milled material circulating during the milling operation in order that the inspection opening and the insert element therein are subjected less strongly to any abrasive stresses.

The invention is suitable for use, for example, in road construction machines or recyclers or stabilizers or surface miners or, generally speaking, in construction machines or mining machines with working drums the condition of which, including the condition of the tools, is to be inspected.

The invention also provides a method for monitoring the condition of a working drum of a construction machine, or mining machine respectively, or of the tools thereof arranged on the circumference of the working drum. The condition of the working drum or of the tools thereof is measured by a monitoring device through at least one inspection opening in a housing shell of a drum housing, said housing shell at least partially enclosing the circumference of the working drum. The at least one inspection opening is closed during the working operation of the working drum or is opened for the duration of the inspection, namely, during the condition measurement, with an interruption of the working operation in which the working drum is not engaged with a surface to be worked. In closed state, the inspection opening is closed with at least one insert element complementary to the inspection opening, said insert element being locked in the closed position in a positive-fitting fashion.

In this arrangement, closing or opening of the at least one inspection opening is effected by means of drive mechanisms which are remote controllable from the operator's platform of the construction machine or mining machine, respectively.

BRIEF DESCRIPTION OF THE DRAWINGS

In the following, one embodiment of the invention is explained in greater detail with reference to the drawings.

The following is shown.

DETAILED DESCRIPTION

Figure 1:
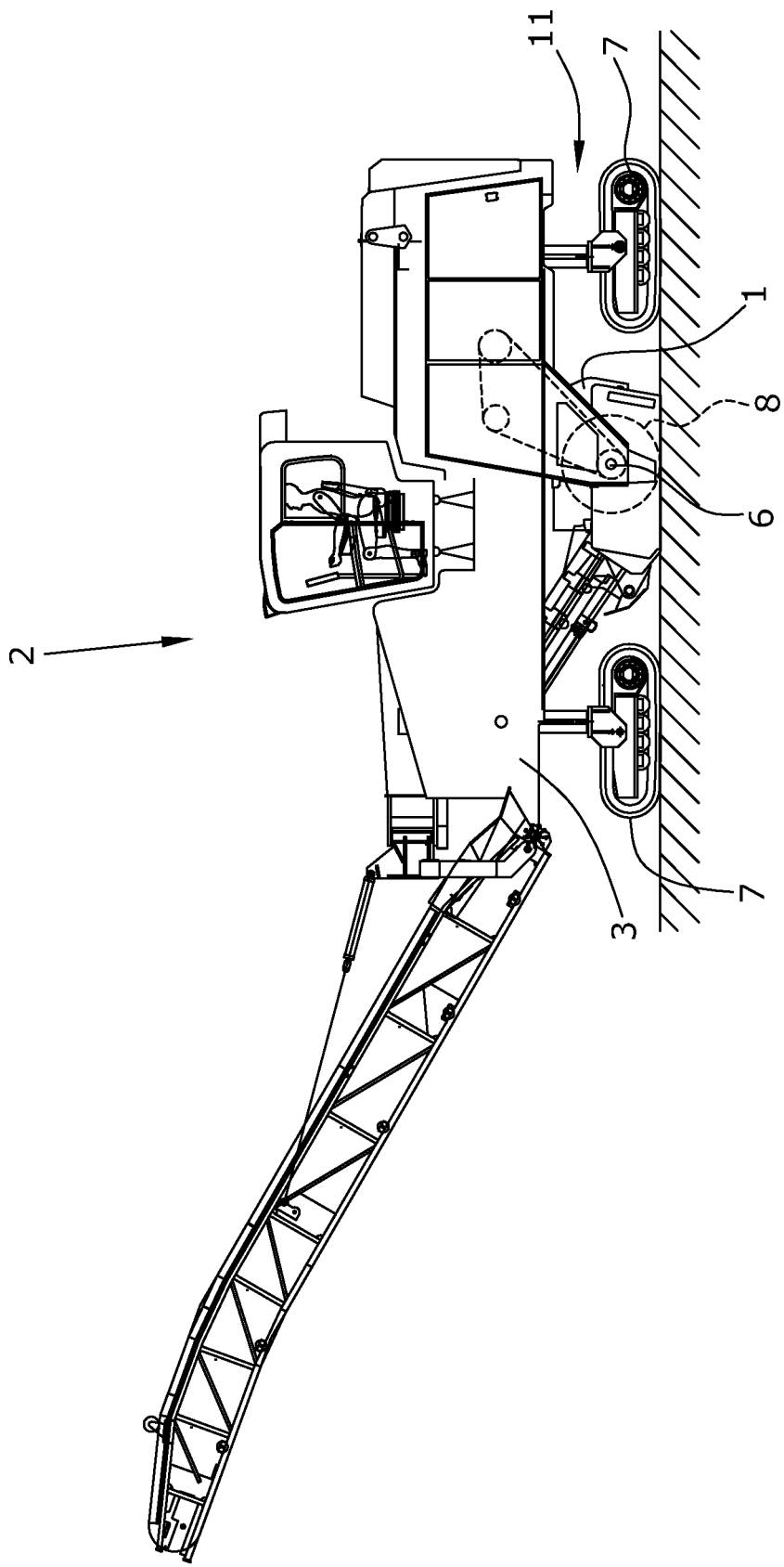
FIG. 1 an example of a construction machine in the design of a road milling machine, FIG. 2 a drum housing with monitoring device in accordance with prior art, FIG. 3 the monitoring device directed at the working drum in accordance with the prior art, FIG. 4*a* a top view of the housing shell of the drum housing with a closing mechanism in closed position, and FIG. 4*b* a closing mechanism in opened position, FIG. 5*a* a cross-section through the inspection openings in the housing shell in closed position of the closing mechanism, FIG. 5*b* a cross-section in accordance with FIG. 5*a* in opened position of the closing mechanism, and FIG. 6*a* a side view of the closing mechanism in circumferential direction of the drum housing in closed position, and FIG. 6*b* a side view of the closing mechanism in circumferential direction of the drum housing in opened position.

FIG. 1 shows an example of a construction machine 2 in the design of a road milling machine for milling ground surfaces or traffic surfaces. The road milling machine comprises a chassis with, for example, four crawler track units 7, which supports the machine frame 3 of the road milling machine. It is understood that the crawler track units 7 may be substituted wholly or in part by wheel units. A working drum 8 rotating about a drum axis 6 is supported in the machine frame 3 in the design of a milling drum fitted with tools 4, said milling drum extending transversely to the direction of travel of the construction machine 2. The working drum 8 is partially enclosed by a drum housing 1. Setting of the milling depth is preferably effected by means of the height adjustment of the crawler track units 7 via lifting columns 11 but may also be effected by a height-adjustable working drum 8 in a height-adjustable drum housing 1.

It is understood that the construction machine 2 with a working drum 8 and a drum housing 1 may also consist of other machines such as, for example, soil stabilizers, cold recyclers, recycling machines, surface miners.

Figure 2:
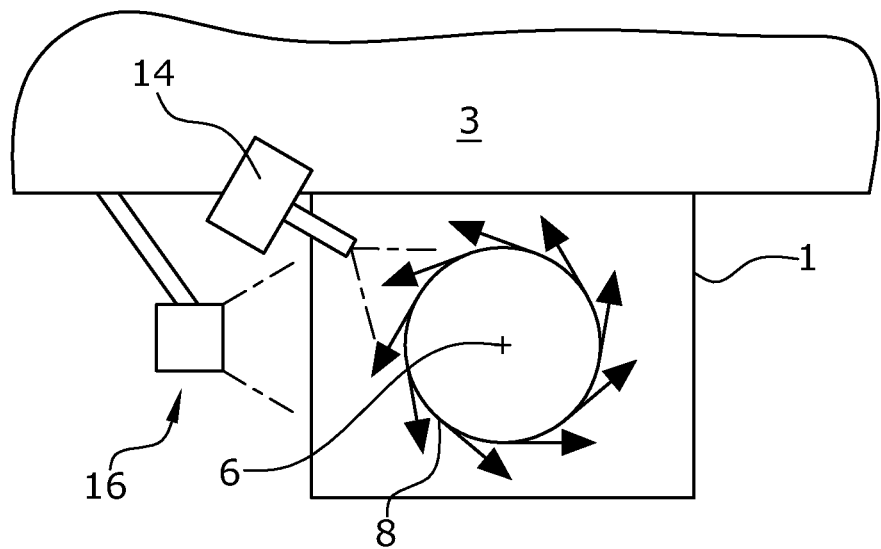

FIG. 2 shows a monitoring device from DE 10 2008 45 470 (US 2010/0076697), mounted at a drum housing 1 and comprising a sensor device 14, for example, an inspection camera, and a light source 16. The inspection camera 14 protrudes, with a barrel, through the drum housing 1 into the mixing chamber enclosing the working drum 8 within the drum housing 1.

Figure 3:
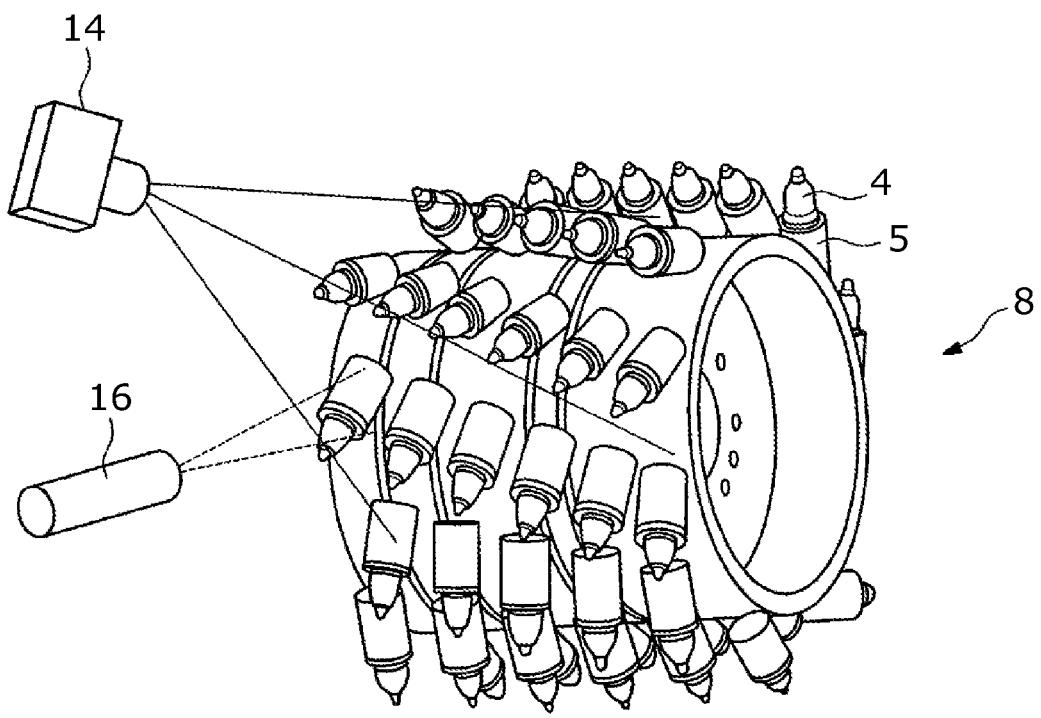

FIG. 3 shows the working drum 8 fitted with tools 4 from DE 10 2008 045 470 (US 2010/0076697), wherein the replaceable tools 4 are mounted in toolholders 5. The arrangement of the inspection camera 14 and the illuminating device 16 is illustrated schematically. It is understood that the illuminating device 16 illuminates the working drum 8 to be inspected, or the tools 4 and toolholders 5 thereof, respectively, in that area in which the sensor device 14 in the design of an inspection camera captures the objects to be monitored. The illuminating device 16 can be dispensed with if sufficient light is available for condition monitoring (inspection). The monitoring device may alternatively consist of, for example, an ultrasonic sensor or, for example, a scanner, preferably a laser scanner.

With respect to an inspection procedure to be performed, reference is made to DE 10 2008 045 470 (US 2010/0076697), the full disclosure content of which is incorporated herein by reference.

Figure 4A:
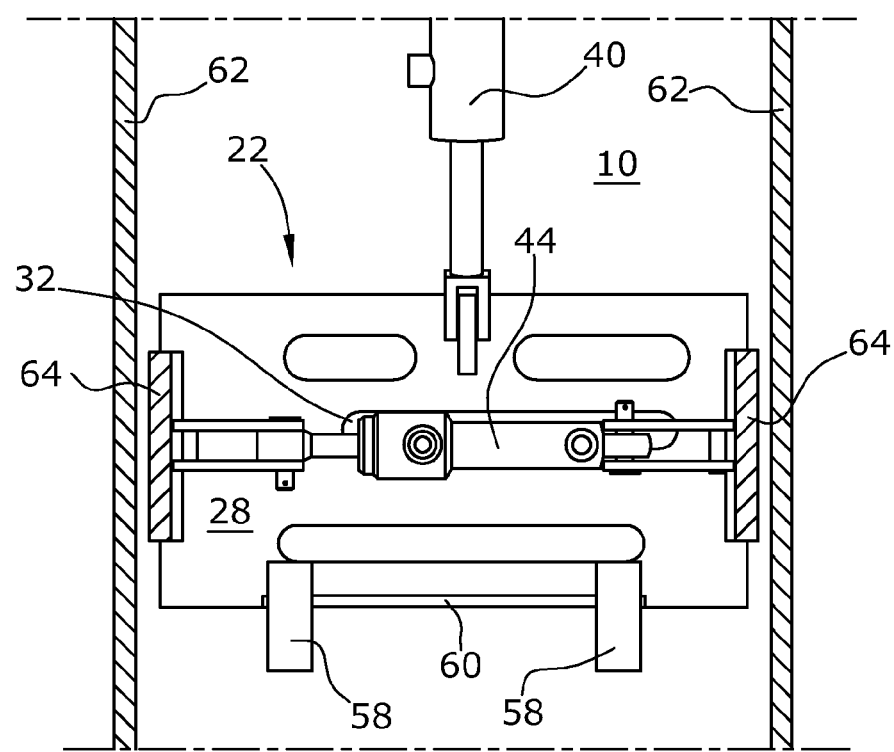
Figure 4B:
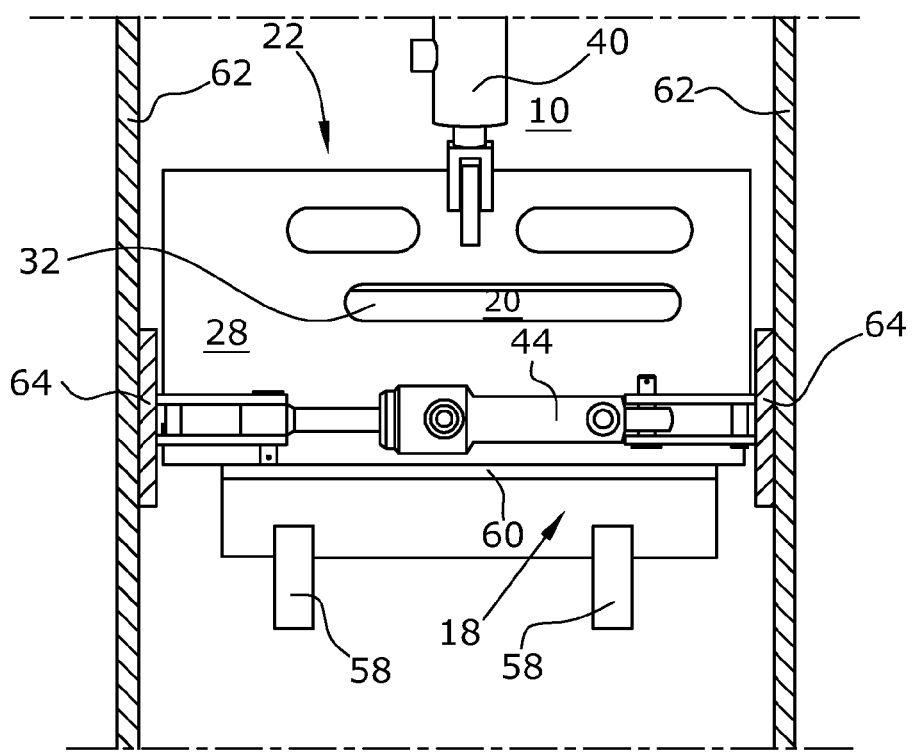

FIGS. 4*a*, 4*b* show a top view of an embodiment of the present invention including a housing shell 10 of the drum housing 1, said housing shell 10 enclosing the circumference of the working drum 8.

Figure 5A:
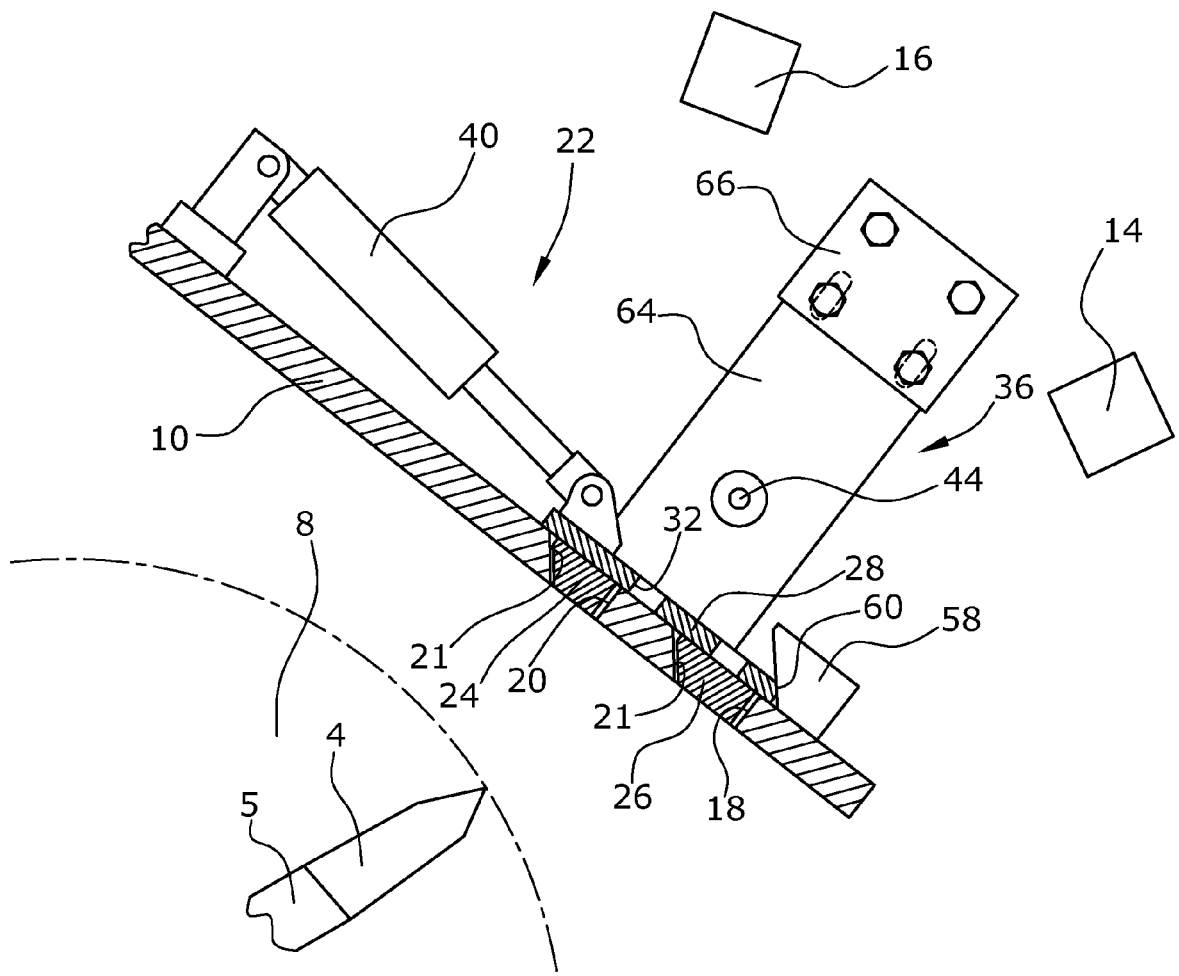
Figure 5B:
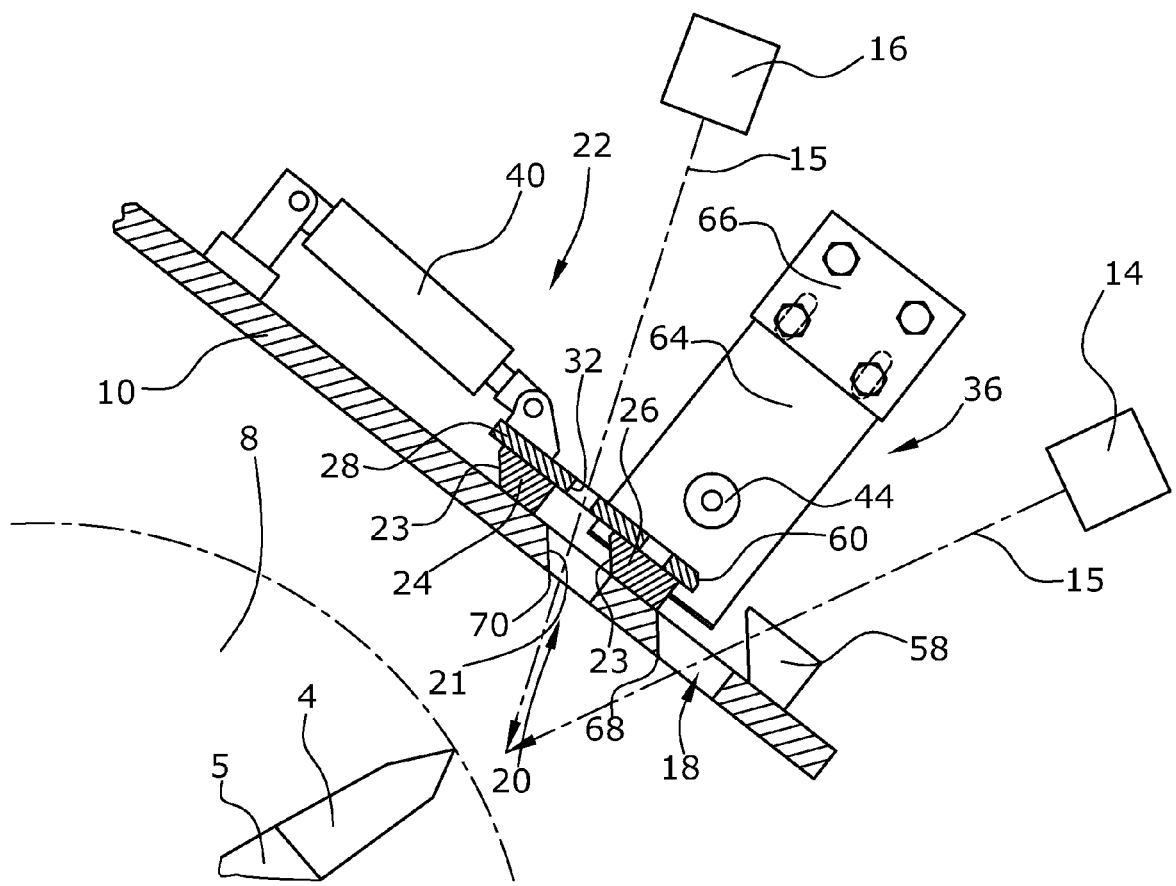

In the housing shell 10, inspection openings 18, 20 apparent from FIG. 4*b* and FIG. 5*b* are provided, which are to permit measuring beams or light beams 15, respectively, of the monitoring device 14, 16 to pass through during the inspection of the working drum 8 and the tools 4 and toolholders 5 thereof. A closing mechanism 22 is arranged on the outside of the housing shell 10 apparent from FIG. 4*a*, said closing mechanism 22 enabling closure of the inspection openings 18, 20. In the event of a very large working width of the working drum 8, for example, 2.50 meters and more, several monitoring devices 14, 16 may be arranged behind one another in longitudinal direction of the working drum 8. The closing mechanism 22 is shown in closed state in FIG. 4*a*, and in opened state in FIG. 4*b*.

The closing mechanism 22 comprises a first drive mechanism 40 which is capable, on the circumference of the housing shell 10 in circumferential direction and transversely to the drum axis 6, of moving a support plate 28 from a closed position as it is depicted in FIG. 4*a* of the working drum 8 into an opened position as it is shown in FIG. 4*b*. For example, the first drive mechanism 40 includes a piston cylinder unit.

On the bottom side of the support plates 28, insert elements 24, 26 are mounted which, as is most evident from FIGS. 5*a* and 5*b*, are capable of engaging with the inspection openings 18, 20 in the housing shell 10 in a preferable positive-fitting fashion. The support plates 28 are guided laterally so that they can be transferred from the closed position into the opened position and vice versa without jamming.

When moved into the closed position, the support plate 28 is shifted, starting from the position in FIGS. 4b and 5b, into the position as it is depicted in FIGS. 4a and 5a. At the end of the path of travel of the first drive mechanism 40, the front leading edge 60 of the support plate 28 when seen in the direction of movement knocks against two wedge-shaped limit stops 58 arranged at a distance from one another, the wedged shape of which pushes the support plate 28, with the insert elements 24, 26 attached thereto, radially inwards so that the insert elements 24, 26 are pushed downwards into the corresponding inspection openings 18, 20. To this effect, the leading edge 60 of the support plate 28 may be provided with a slanted edge adapted to the wedged shape of the limit stops 58. The position of the support plate 28 with the insert elements 24 and 26 in closed position is most evident in FIG. 5a.

If the closed inspection openings 18, 20 are to be released for an inspection, the closing mechanism 22 is moved in opposite direction by way of the drive mechanism 40 moving the support plate 28 towards itself. The inspection openings, namely the first opening 18 for the sensor device 14 and the second opening 20 for the light source 16, each comprise slanted surfaces 21 on the side facing away from the limit stops 58, said slanted surfaces 21 running, for example, at an angle of 45 degrees to the surface of the housing shell 10. The insert elements 24, 26 comprise slanted surfaces 23 complementary thereto so that, when the first drive mechanism exerts a tensile force on the support plate 28, the slanted surfaces 23 glide on top of the slanted surfaces 21 and, in doing so, lift the support plate while transferring it into its opened position at the same time.

In the end position of the opened position as evident from FIG. 5b, the inspection openings, i.e. in detail, the inspection openings 18 and 20, are released so that the inspection camera 14 can inspect the working drum 8 or the tools 4 or toolholders 5, respectively, thereof through the inspection opening 18. A light source may illuminate the objects to be examined through the inspection opening 20. To ensure that the light can pass through, the support plate comprises at least one opening 32 which is adapted to the inspection opening 20.

The closing mechanism 22 may additionally be provided with a locking mechanism 36 which is evident in particular from FIGS. 4a, 4b, 6a and 6b.

Similar to FIGS. 4a, 4b, FIGS. 6a, 6b show the locking mechanism 36 in locked state and in a state in which the support plate 28 is released. The locking mechanism 36 comprises a second drive mechanism 44 which runs transversely, orthogonally in the embodiment of the invention, to the first drive mechanism 40. The locking mechanism 36 causes the support plate 28 to be lockable, in closed position of the closing mechanism 22, in radial direction.

The locking mechanism 36 comprises two plate-shaped devices 64 supported at the drum housing 1, said devices 64 resting, in the locked position, with one free end on the support plate 28 while the other end is supported in a pocket 67 in a bracket 66 mounted at the drum housing 1. The plate-shaped devices are each connected, via a joint 45, with the second drive mechanism 44.

To this effect, the drum housing 1 comprises partition walls 62 projecting orthogonally from the housing shell 10, said partition walls 62 serving the purpose, among other things, of stiffening the drum housing 1. Furthermore, the drum housing 1 has frontal outer walls. As is most evident from FIGS. 6a and 6b, brackets 66 are mounted at the partition walls 62 or at the outer walls respectively, said brackets 66 forming a pocket 67 in which the plate-shaped device 64 is received with one end. The plate-shaped device 64 is supported in the pocket 67 in an articulated fashion and can be pivoted about a small angle by means of the second drive mechanism 44. In the released position depicted in FIG. 6b, the plate-shaped device 64 rests, on both sides, at a partition wall 62 or a frontal outer wall respectively, by way of the second drive mechanism 44 being transferred into its extended position. In this case, the plate-shaped devices 64 do not rest on the support plate 28, consequently releasing the latter in radial direction so that the support plate 28, when operating the first drive mechanism 40, can be lifted towards the opened position in order for the insert elements 24, 26 to be able to come out of the inspection openings 18, 20 and release the inspection openings for an inspection to be performed.

This position is also apparent in FIG. 4b in top view.

Figure 6A:
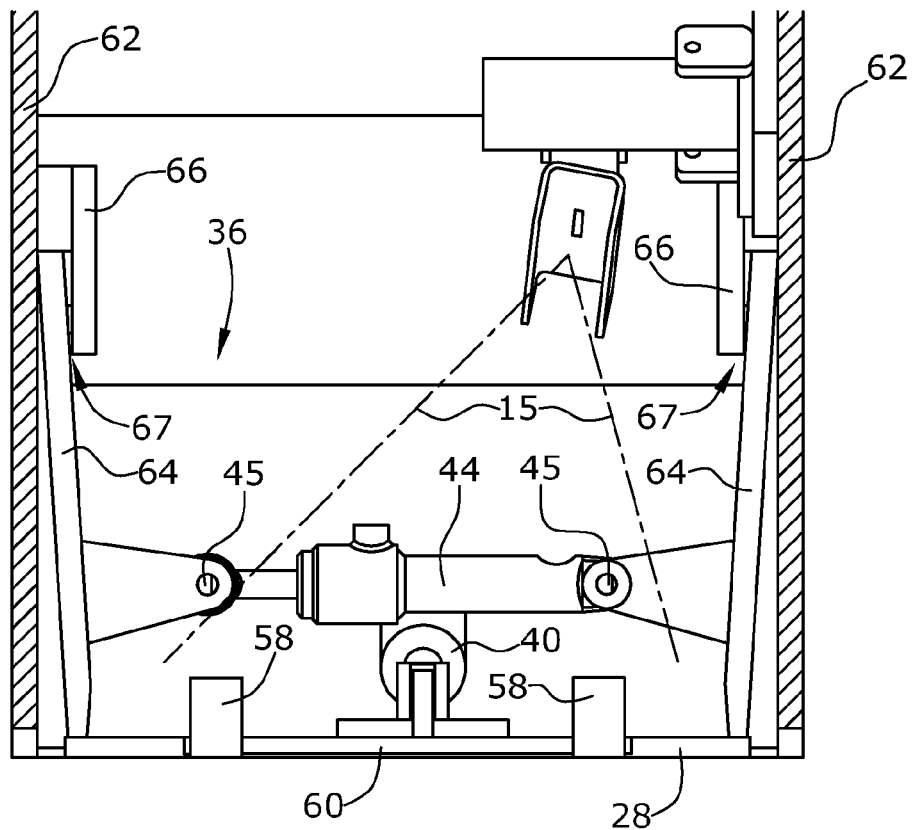
Figure 6B:
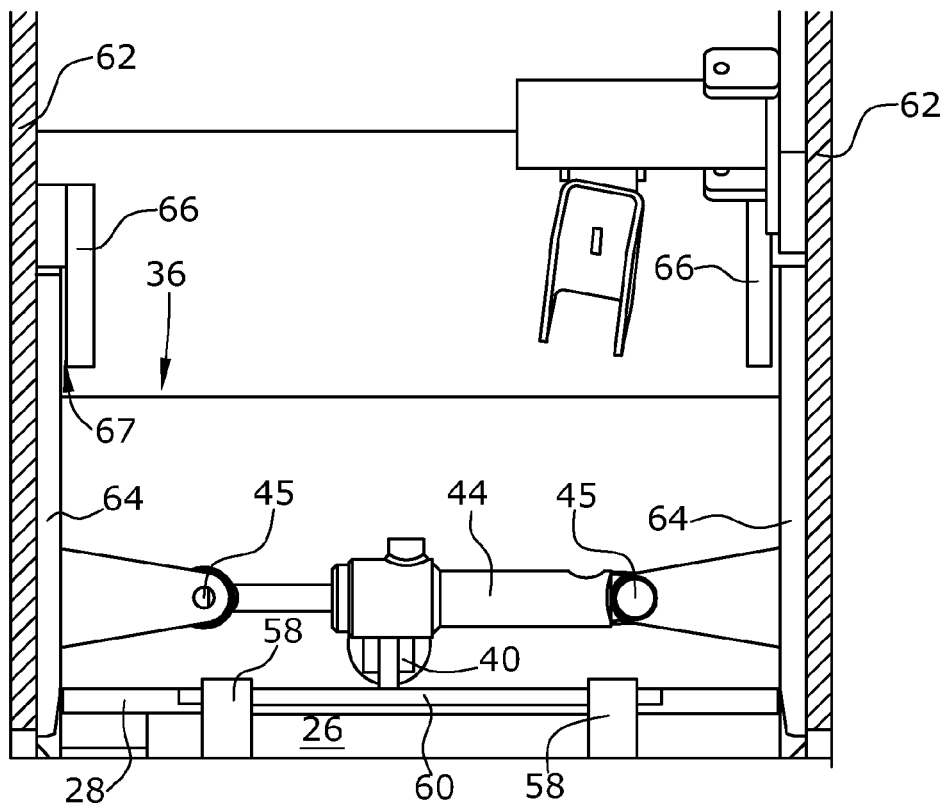

In the closed position depicted in FIGS. 4a and 6a, the plate-shaped devices 64 are moved towards one another by contraction of the second drive mechanism 44. When the support plate 28 on the housing shell 10 is in the closed position, the plate-shaped devices 64 can rest themselves, at their radially inner end, on the support plate 28 whereby the latter is supported in radial direction. Owing to the rigid radial support of the support plate 28, no shocks occurring during the milling operation can be transferred to the insert elements 24, 26 to the drive mechanisms 40, 44 as the drive mechanisms 40, 44 do not need to absorb any forces whatsoever and the support plate 28 is locked with the drum housing 1 in a positive-fitting manner or is locked at the drum housing 1.

Although the invention has been described and illustrated with reference to specific illustrative embodiments thereof, it is not intended that the invention be limited to those illustrative embodiments. Those skilled in the art will recognize that variations and modifications can be made without departing from the true scope of the invention as defined by the claims that follow. It is therefore intended to include within the invention all such variations and modifications as fall within the scope of the appended claims and equivalents thereof.

What is claimed is:

1. A drum housing for a working drum of a construction machine or mining machine, said working drum being provided with tools and rotating about a drum axis, with a housing shell which at least partially encloses the circumference of the working drum, and with at least one inspection opening arranged in the housing shell for a monitoring device, wherein said monitoring device inspects the condition of the working drum or the tools thereof, further comprising:
a closing mechanism including a sliding plate arranged outside of the housing shell, said sliding plate being slidable between a closed position wherein the sliding plate blocks a viewing path between the monitoring device and the at least one inspection opening, and an open position wherein the viewing path is open such that the monitoring device can view the working drum or the tools thereof through the at least one inspection opening.

2. The drum housing in accordance with claim 1, wherein the at least one inspection opening in the housing shell extends in a longitudinal direction of the working drum.

3. The drum housing in accordance with claim 1, wherein the at least one inspection opening tapers radially towards the working drum.

4. The drum housing in accordance with claim 1, wherein the monitoring device comprises at least one sensor device and the at least one inspection opening comprises at least one opening for the sensor device.

5. The drum housing in accordance with claim 1, wherein the monitoring device comprises at least one sensor device and at least one illuminating device and wherein the at least one inspection opening comprises at least one first opening for the sensor device and at least one second opening for the illuminating device.

6. The drum housing in accordance with claim 1, wherein the closing mechanism comprises at least one insert element adapted to the at least one inspection opening in a complementary fashion, said at least one insert element engaging with the at least one inspection opening to close the at least one inspection opening.

7. The drum housing in accordance with claim 6, wherein the at least one insert element is arranged on the sliding plate.

8. The drum housing in accordance with claim 7, wherein the sliding plate comprises at least one passage opening which allows, in the open position of the sliding plate, the passage of light beams and/or measuring beams of the monitoring device through the at least one passage opening of the sliding plate and the at least one inspection opening in the housing shell.

9. The drum housing in accordance with claim 7, wherein the closing mechanism comprises a locking mechanism and the sliding plate with the at least one insert element is lockable, in the closed position of the sliding plate, in radial direction by the locking mechanism.

10. The drum housing in accordance with claim 9, wherein the locking mechanism comprises at least one device supported at the drum housing which, in the closed position of the sliding plate, supports the sliding plate, in the closed position of the sliding plate, in a positive-fitting fashion radially outwards and, for the purpose of moving the sliding plate into the open position, releases the sliding plate for shifting.

11. The drum housing in accordance with claim 6, wherein the at least one insert element is locked radially outwards in the closed position of the sliding plate.

12. The drum housing in accordance with claim 6, wherein the closing mechanism comprises a first drive mechanism, wherein the first drive mechanism moves the at least one insert element between the closed position and open position on the outside of the housing shell.

13. The drum housing in accordance with claim 12, wherein the first drive mechanism, when moved in closing direction, pushes the at least one insert element, which is supported by the sliding plate, into the at least one inspection opening by engagement between at least one wedge-shaped limit stop mounted on the housing shell and one leading edge at a front end of the sliding plate when seen in the direction of movement, said leading edge being adapted to the wedged shape of the at least one limit stop.

14. The drum housing in accordance with claim 12, wherein the at least one insert element and the corresponding at least one inspection opening comprise slanted sides adapted to one another such that the first drive mechanism, when moved in opening direction, moves the at least one insert element out of the at least one inspection opening.

15. The drum housing in accordance with claim 1, wherein a plurality of inspection openings and corresponding closing mechanisms are arranged next to one another across width of the working drum.

16. A construction machine, comprising a working drum and a drum housing in accordance with claim 1.

17. A method for monitoring the condition of a working drum of a construction machine or mining machine or of the tools thereof arranged on the circumference of the working drum by measuring the condition of the working drum or the tools thereof by means of a monitoring device through at least one inspection opening in a housing shell of a drum housing, said housing shell at least partially enclosing the circumference of the working drum, the method comprising:

(a) closing the at least one inspection opening during the working operation of the working drum and opening the inspection opening for the duration of the condition measurement, with an interruption of the working operation in which the working drum is not engaged with a surface to be worked, wherein the at least one inspection opening, in closed condition, is closed with at least one insert element complementary to the corresponding inspection opening, said insert element being locked in the closed position in a positive-fitting fashion;

(b) opening the at least one inspection opening; and (c) inspecting the condition of the working drum or the tools thereof through the at least one inspection opening with the monitoring device located outside of the at least one inspection opening.

18. A construction machine apparatus, comprising:
a working drum including working tools, the drum having a circumference and being rotatable about a drum axis;
a drum housing including a housing shell at least partially enclosing the circumference of the working drum, the housing shell including a first inspection opening therein;
a monitor arranged outside of the inspection opening to inspect the working tools through the inspection opening;
a closure; and
a powered actuator arranged to move the closure between a closed position wherein the closure closes the inspection opening, and an open position wherein the inspection opening is open.

19. The apparatus of claim 18, wherein the inspection opening extends in a longitudinal direction parallel to the drum axis.

20. The apparatus of claim 18, wherein the inspection opening tapers radially inwards toward the working drum.

21. The apparatus of claim 18, wherein:
the housing shell further includes a second inspection opening; and
the monitor includes a sensor arranged outside of the first inspection opening to inspect the working tools through the first inspection opening, and an illumination source arranged to illuminate the working tools through the second inspection opening.

22. The apparatus of claim 18, wherein:
the closure includes an insert element shaped complementary to the inspection opening, so that the insert element can be received in the inspection opening to close the inspection opening.

23. The apparatus of claim 22, wherein:
the closure includes a support plate, and the insert element is attached to the support plate, the support plate being slidable between an open position and a closed position to open and close the inspection opening.

24. The apparatus of claim 23, wherein:
the support plate has a passage opening defined therethrough, the passage opening being aligned with the monitor and the inspection opening when the support plate is in the open position.

25. The apparatus of claim 23, further comprising:
a lock arranged to engage a radially outer side of the support plate and to lock the support plate in its closed position.

26. The apparatus of claim 23, further comprising:
a limit stop attached to the housing shell, the limit stop having a tapered surface; and
wherein the support plate includes a leading edge arranged to engage the tapered surface of the limit stop as the support plate is moving to its closed position, such that the support plate and the insert element are moved radially inward to push the insert element into the inspection opening.

27. The apparatus of claim 18, wherein:

the closure includes a sliding plate: and the powered actuator is arranged to slide the sliding plate between the closed position of the closure and the open position of the closure.

* * * * *